United States Patent
Harthorn et al.

(10) Patent No.: US 7,234,347 B2
(45) Date of Patent: Jun. 26, 2007

(54) INTERNAL RISER INSPECTION DEVICE AND METHODS OF USING SAME

(75) Inventors: Larry K. Harthorn, Conroe, TX (US); Christopher B. Disher, Lafayette Parish, LA (US)

(73) Assignee: Vetco Gray Inc., Houston, TX (US)

( * ) Notice: Subject to any disclaimer, the term of this patent is extended or adjusted under 35 U.S.C. 154(b) by 0 days.

(21) Appl. No.: 11/496,160

(22) Filed: Jul. 31, 2006

(65) Prior Publication Data

US 2006/0260391 A1  Nov. 23, 2006

Related U.S. Application Data

(63) Continuation of application No. 10/805,709, filed on Mar. 22, 2004, now Pat. No. 7,082,822, which is a continuation-in-part of application No. 10/351,569, filed on Jan. 24, 2003, now Pat. No. 6,904,818.

(60) Provisional application No. 60/370,444, filed on Apr. 5, 2002.

(51) Int. Cl.
  *E21B 33/00* (2006.01)
  *G01N 29/04* (2006.01)
  *A61B 5/04* (2006.01)
(52) U.S. Cl. ............... 73/152.57; 73/623; 73/865.8
(58) Field of Classification Search ............. 73/152.57, 73/865.8, 598, 623
See application file for complete search history.

(56) References Cited

U.S. PATENT DOCUMENTS 3,810,384 A   5/1974  Evans
4,055,990 A   11/1977 Topping
4,162,635 A   7/1979  Triplett et al.
4,213,345 A   7/1980  Dufour
4,218,923 A   8/1980  Triplett et al.
4,285,242 A   8/1981  Braithwaite (Continued)

FOREIGN PATENT DOCUMENTS

EP    0304053    2/1989

(Continued)

OTHER PUBLICATIONS

R. van Agthoven, Ultrasonic Inspection of Risers a New and Simple Approach, Nov. 1998.

*Primary Examiner*—Hezron Williams
*Assistant Examiner*—John Fitzgerald
(74) *Attorney, Agent, or Firm*—Bracewell & Giuliani LLP

(57) ABSTRACT

An inspection apparatus includes an inspection unit that is lowered into vertically supported pipe filled with seawater. The apparatus includes a pipe weld location detector module carried by the inspection unit. The apparatus also includes a rotating time of flight diffusion (TOFD) module and a non-rotating wall thickness module carried by the inspection unit. The module includes a pair of rotatably mounted weld volume inspection transducers rotatable by an operator and adapted to inspect for and obtain data on weld volume defects. The TOFD module has a fluid carrier positioned within the TOFD module and contains an acoustic fluid. The non-rotating wall thickness module also contains an acoustic liquid and includes a plurality of fixedly mounted wall inspection transducers adapted to obtain data on wall thickness of a portion of the pipe.

10 Claims, 7 Drawing Sheets

U.S. PATENT DOCUMENTS

| | | |
|---|---|---|
| 4,285,243 A | 8/1981 | Collingwood |
| 4,375,165 A | 3/1983 | De Sterke |
| 4,641,529 A | 2/1987 | Lorenzi et al. |
| 4,663,727 A | 5/1987 | Saporito et al. |
| 4,772,849 A | 9/1988 | Tedder |
| 4,876,672 A | 10/1989 | Petermann et al. |
| 4,964,059 A | 10/1990 | Sugaya et al. |
| 5,099,692 A | 3/1992 | Lodder et al. |
| 5,175,964 A | 1/1993 | Girndt |
| 5,285,689 A | 2/1994 | Hapstack et al. |
| 5,385,049 A | 1/1995 | Hunt et al. |
| 5,392,527 A | 2/1995 | Ziskovsky et al. |
| 5,454,267 A | 10/1995 | Moreau et al. |
| 5,574,223 A | 11/1996 | Kiefer |
| 5,587,534 A | 12/1996 | McColskey et al. |
| 5,661,241 A | 8/1997 | Harth, III et al. |
| 5,675,084 A | 10/1997 | Goedecke |
| 5,770,800 A | 6/1998 | Jenkins et al. |
| 2002/0134178 A1 | 9/2002 | Knight et al. |
| 2003/0188589 A1 | 10/2003 | Harthorn et al. ........... 73/865.8 |

FOREIGN PATENT DOCUMENTS

| | | |
|---|---|---|
| EP | 0684446 A3 | 11/1995 |
| GB | 2385129 | 6/2002 |
| WO | WO 02/44709 | 6/2002 |

INTERNAL RISER INSPECTION DEVICE AND METHODS OF USING SAME

RELATED APPLICATIONS

This application is a continuation of application Ser. No. 10/805,709, filed Mar. 22, 2004, now U.S. Pat. No. 7,082,822, issued Aug. 1, 2006, which is a continuation-in-part of application Ser. No. 10/351,569, filed Jan. 24, 2003, now U.S. Pat. No. 6,904,818, issued Jun. 14, 2005, which claims priority from the provisional application Ser. No. 60/370,444, filed Apr. 5, 2002 titled "Internal Riser Inspection Device."

BACKGROUND OF THE INVENTION

1. Field of the Invention

The invention relates in general to non-destructive testing of pipe, and in particular to a test unit that is conveyed internally through pipe for ultrasonically inspecting the pipe wall thickness and welds and methods for inspecting associated therewith.

2. Description of the Related Art

Non-destructive testing of pipe has been done for many years utilizing ultrasonic transducers, eddy current measurements, x-ray and other techniques. Operators using pulse echo techniques with ultrasonic transducers or probes can determine wall thickness, which is a measure of any corrosion that has occurred. One favorite technique is to propel a vehicle or "pipeline pig" through the pipeline to examine the walls of the pipe using the ultrasonic probes. For welds, operators have used time of flight diffraction ("TOFD") techniques with ultrasonic transducers. Also, a method known as pulse echo shear wave has been combined with TOFD transducer measurements to inspect portions of the weld that are missed by the TOFD transducer.

One type of pipe that requires periodic inspection is a drilling riser. Drilling risers, which are utilized for offshore drilling, extend from the drilling rig to a blowout preventer and Lower Marine Riser Package (LMRP), which connect to a subsea wellhead. Drilling risers are made up of sections joined together with various types of connectors, each section being typically from 5–90 feet in length. Each drilling riser section has a central riser pipe that is normally about 18–24 inches in diameter. Several auxiliary lines are mounted to the exterior of the central riser pipe, the auxiliary lines being used for a choke, kill and hydraulic boost purposes. The auxiliary lines are smaller in diameter and mounted parallel and offset to the axis of the central riser pipe. Normally there will be at least one weld within each riser section, this being a center weld that connects two tubular pipes together to form the riser section. Also, normally the connectors are mounted to the ends of the riser sections by welding. Many risers also have buoyant jackets mounted to the exterior.

A drilling vessel may have several thousand feet of riser pipe, depending on the depth to which it is rated. During use, drill pipe with drill bits on the end, casing, and other well tools are lowered through the riser. Drilling mud returns up the riser. The auxiliary lines are pressurized for various purposes from time to time. The drilling riser is re-used after each well. Consequently it is necessary to periodically inspect the riser to make sure that it has no weaknesses that could result in leakage or pipe failure.

Inspection in the past has been done primarily by "pulling" the riser string, disconnecting each riser section from adjacent sections, and transporting the riser sections to a facility on land that performs the inspection services. The facility removes the buoyancy jackets and auxiliary lines from each section. The riser sections are cleaned and inspected from the exterior with various ultrasonic transducers. If the riser has a coating of any type, it must be removed at each inspection site. After inspection, the riser sections are reassembled and shipped back to the drilling vessel. It is time consuming and expensive to transport, clean, disassemble, inspect and reassemble the riser sections. During this time, unless a spare drilling riser can be obtained, the drilling rig would not be able to operate. Drilling rigs are very costly on a daily basis.

It has been proposed to inspect the drilling risers at the drilling vessel. Many drilling vessels have the ability to stack the riser sections horizontally on the vessel while not in use. However, there are a number of problems in doing so. The interior of the drilling riser is often not very clean, and may be coated with dried drilling mud. The central riser pipe is often out of round (not cylindrical) in portions. The welded areas of the central pipe may be misaligned slightly. Also, there is normally not much access room on the drilling rig at the ends of each riser section for staging the equipment necessary to do the inspection. Additionally, the riser sections often do not contain flaws and thus are subjected to unnecessary stress caused by the disassembly, inspection, and reassembly of the riser sections.

Thus, recognized is the need for an internal riser inspection device that can perform both a wall thickness and welded defect analysis on a deployed drilling riser. Also recognized is the need for an internal riser inspection device capable of withstanding high operating depth pressure and a wide array of temperatures and capable of being run on a wire line.

SUMMARY OF THE INVENTION

In view of the foregoing, embodiments of the present invention advantageously provide an inspection system which includes an inspection apparatus that is wireline deployable within a bore of a riser pipe section of a deployed drilling riser pipe. For example, in an embodiment of the present invention, an apparatus for inspecting vertically supported pipe includes an inspection unit having a longitudinal axis and adapted to be connected to a line for lowering into and retrieving from the pipe. The inspection unit can include a housing having a proximal end, a distal end, a housing body positioned there between, and an inner housing chamber formed in the housing body.

A wireline extending between the housing of a remote wireline spool is remotely positioned on the deployment platform for raising and lowering the inspection unit. A centralizer can be connected to an external surface of the housing body. The centralizer is adapted to conform to varying pipe inner diameter sizes and has an outer periphery for slidingly contacting the pipe as the inspection unit moves through the pipe. This allows the inspection unit to have a much smaller outer diameter than the inner diameter of the pipe being inspected. The centralizer also can maintain the inspection unit substantially in the center of the inner diameter of the pipe, and can maintain the longitudinal axis of the inspection unit substantially aligned with a longitudinal axis of the pipe. An umbilical cord including a data conductor can be positioned between the proximal end of the housing and a controller remotely positioned on a deployment platform. An umbilical spool can, in turn, be positioned on the deployment platform for storing and deploying the umbilical cord.

A rotating time of flight diffusion (TOFD) module is carried by the inspection unit and is preferably positioned within the inner housing chamber. The module includes a pair of rotatably mounted weld volume inspection transducers adapted to inspect for and obtain data on weld volume defects, and which rotate during inspection at a circumscribed diameter that is less than the diameter of the centralizer at the periphery. The module can also include a rotatable shaft positioned parallel to the longitudinal axis of the housing. A pair of weld volume inspection transducer mounts can be connected to the rotatable shaft. Correspondingly, each of the weld volume inspection transducers can be connected to one of the weld volume inspection transducer mounts. The module is surrounded by a fluid carrier positioned within the inner housing chamber of the inspection unit. The weld volume inspection transducers rotate in sliding contact with an inner diameter of the fluid carrier. An acoustic fluid further provides a liquid coupling between each of the pair of weld volume inspection transducers and the housing.

A wall thickness module is also carried by the inspection unit and preferably positioned within the inner housing chamber. The wall thickness module includes a plurality of preferably nonrotating and fixedly mounted ultrasonic wall inspection transducers that are adapted to obtain data on wall thickness of a portion of the pipe. The wall thickness inspection transducers during inspection are located at a circumscribed diameter less than the diameter of the centralizer at the periphery. A housing surrounding the wall thickness module contains an acoustic fluid to provide a liquid coupling between each of the wall thickness inspection transducers and the housing.

Embodiments of the present invention also include methods of inspecting a vertically supported drilling riser. For example, according to an embodiment of the present invention, the riser is lowered from a platform into seawater and seawater is allowed to enter the riser. The operator then disconnects a lower marine riser package of the drilling riser from a blowout preventer and flushes an inner diameter of the drilling riser with a cleansing fluid such as seawater. The operator then deploys an inspection apparatus into the vertically supported drilling riser containing preferably seawater. The inspection apparatus includes at least one but preferably a plurality of acoustical transducers. The operator centralizes the inspection apparatus in the drilling riser with the transducer spaced inward from a wall of the riser by an annular clearance. The inspection unit can include a plurality of fixedly mounted ultrasonic wall inspection transducers for determining wall thickness of a portion of the drilling riser and a plurality of rotatably mounted weld volume inspection transducers, rotatable about a longitudinal axis of the inspection apparatus, for inspecting weld volume defects. The operator can periodically cause the wall thickness transducers to emit an acoustical signal through the seawater in the annular clearance and into the wall of the drilling riser and detect a return acoustical signal from the wall of the drilling riser to determine wall thickness. The operator can then either take wall thickness readings on the way down or on the way back up, however, taking the wall thickness readings on the way down is the preferred methodology. Periodically, the internal pressure within the inspection apparatus can be equalized with the hydrostatic pressure in an inspection area through use of acoustic liquid. This can be accomplished by flooding the inspection apparatus housing with a liquid.

Once reaching the bottom of the drilling riser, the inspection apparatus can be retracted and can inspect the welds of the drilling riser. Upon reaching a weld inspection site, the operator stops vertical movement along a longitudinal axis of the drilling riser, then rotates the plurality of weld volume inspection transducers about a radial axis of the inspection apparatus. The operator positions the inspection apparatus in a location or position that places a first and a second weld volume inspection transducer on opposite sides of a weld, then simultaneously rotates the first and the second weld inspection transducers, causing the first weld inspection transducer to emit an acoustical signal into the weld and the second weld inspection transducer to receive a return acoustical signal. The operator collects data at each inspection site while the plurality of weld volume inspection transducers are rotated to determine if a volume of the weld has any defects.

The operator can then extract data from the inspection apparatus to determine whether a section of the drilling riser requires additional inspection and repair based upon the severity of any determined defect. If one so exists, the operator can recover, for additional inspection and repair, only those sections of the drilling riser determined to have a severe defect and need only incidentally recover those sections located above a lowest section of those sections determined to require recovery.

BRIEF DESCRIPTION OF THE DRAWINGS

So that the manner in which the features, advantages and objects of the invention, as well as others which will become apparent, are attained and can be understood in more detail, a more particular description of the invention briefly summarized above may be had by reference to the embodiment thereof which is illustrated in the appended drawings, which drawings form a part of this specification. It is to be noted, however, that the drawings illustrate only a preferred embodiment of the invention and is therefore not to be considered limiting of its scope as the invention may admit to other equally effective embodiments.

DETAILED DESCRIPTION

The present invention will now be described more fully hereinafter with reference to the accompanying drawings which illustrate embodiments of the invention. This invention may, however, be embodied in many different forms and should not be construed as limited to the illustrated embodiments set forth herein. Rather, these embodiments are provided so that this disclosure will be thorough and complete, and will fully convey the scope of the invention to those skilled in the art. Like numbers refer to like elements throughout, and the prime notation, if used, indicates similar elements in alternative embodiments.

Figure 1:
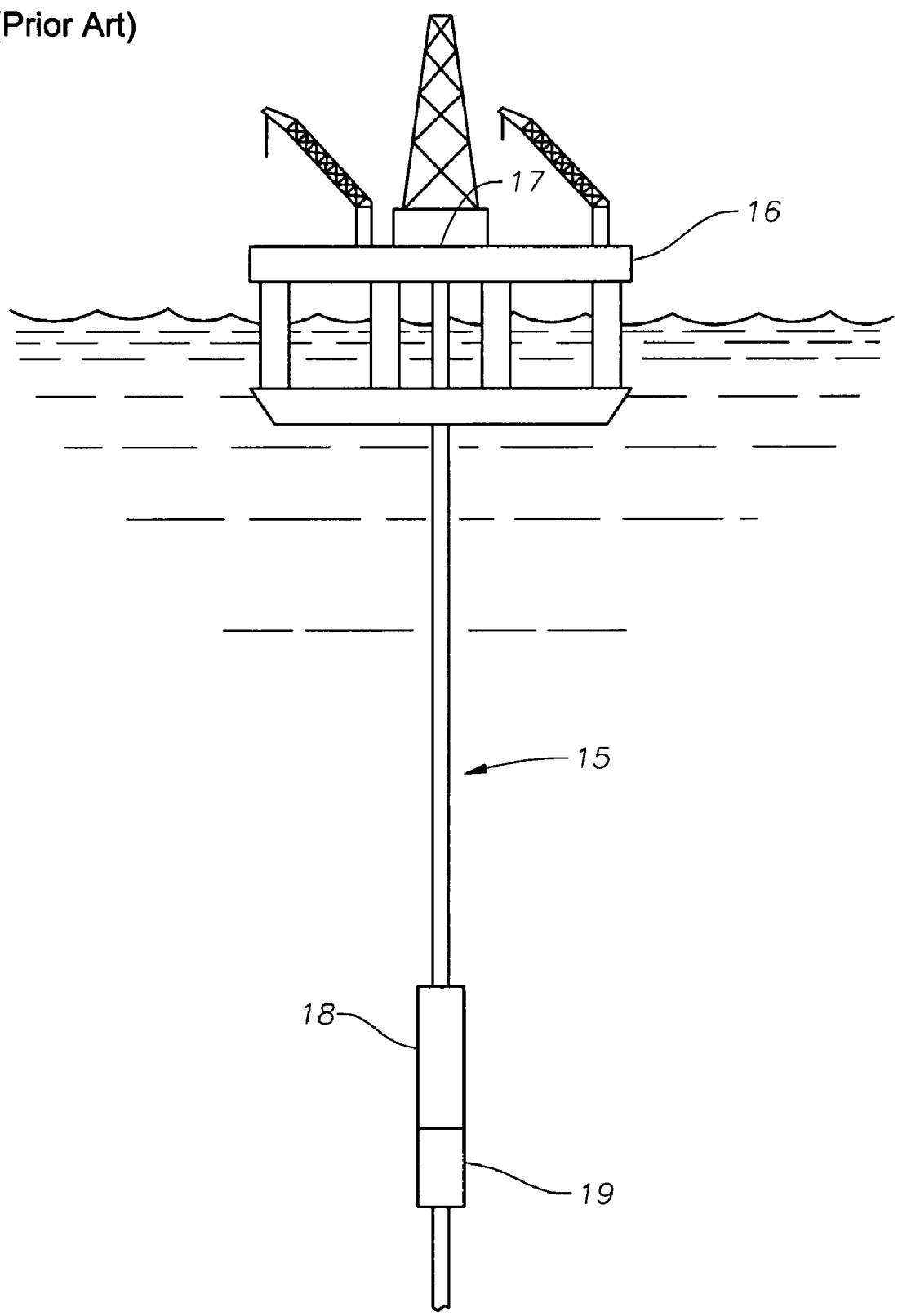
FIG. 1 is a perspective view of a prior art floating platform having deployed drilling riser.

Referring to FIG. 1, shown is a deployed drilling riser pipe 15 extending between a floating vessel having an operational platform 16 and the sea bottom (not shown). A spider 17, located on the operational platform 16, provides support to a proximal end of the deployed drilling riser pipe 15. The deployed drilling riser pipe 15 is further connected at its distal end to a lower marine riser package 18 ("LMRP"). The LMRP 18 is releasably connected to a blowout preventer ("BOP") 19. A diverter (not shown) is located at the upper end of riser 15 and has an elastomeric element that closes around a section of pipe of the drilling riser pipe 15. A side outlet of the diverter delivers the drilling fluid to equipment for clearing the drilling fluid as it circulates.

Figure 2:
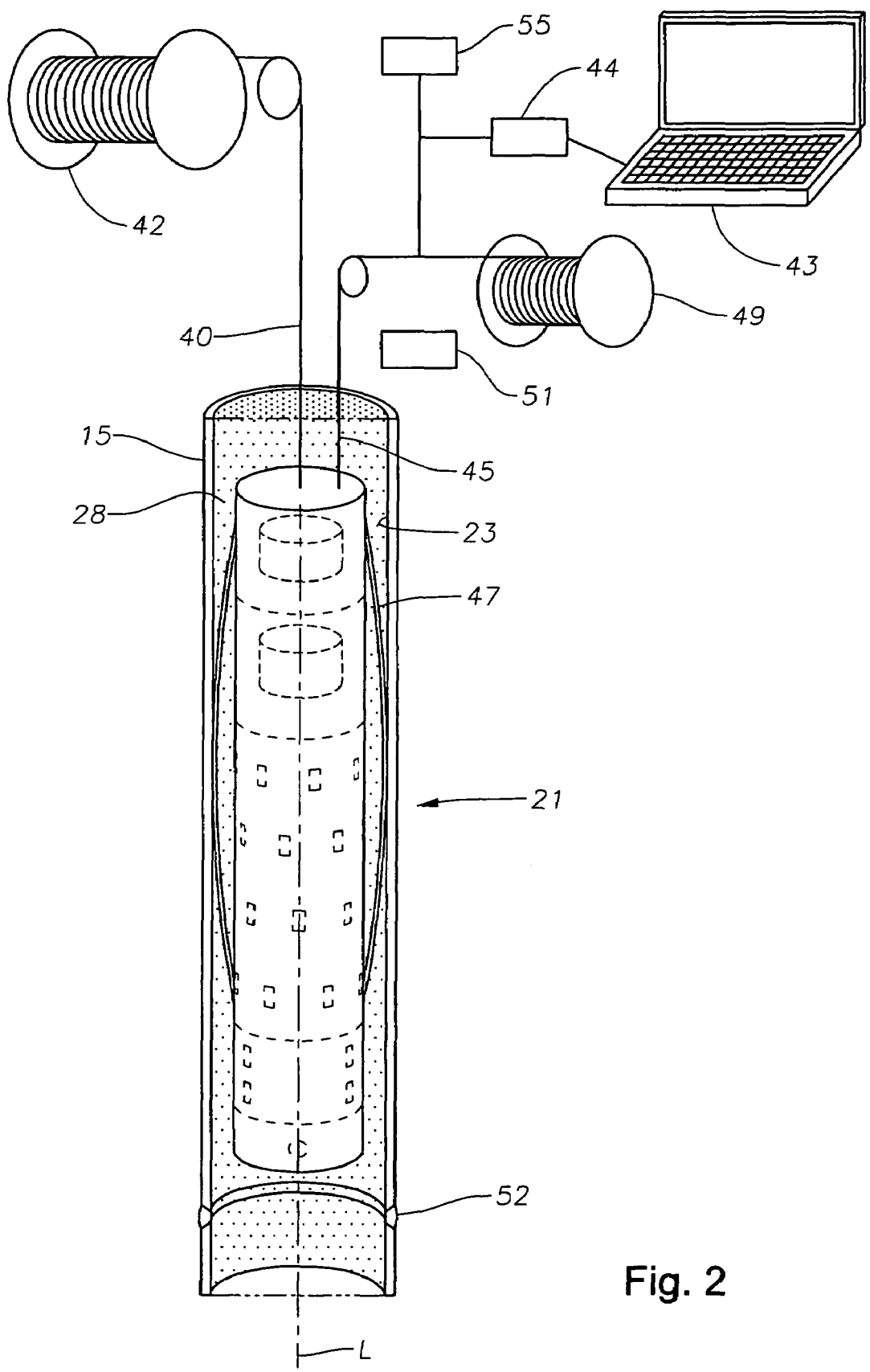
FIG. 2 is a schematic diagram of a system to inspect the vertically supported drilling riser pipe of FIG. 1, according to an embodiment of the present invention.

As perhaps best shown in FIG. 2, the inspection system of this invention includes an inspection apparatus 21 that is wireline deployable within a bore 23 of a riser pipe section of the deployed drilling riser pipe 15. This deployment, further described later, is preferably accomplished by either deploying the inspection apparatus 21 through a diverter (not shown) or on the drilling riser pipe 15 while hung off a spider 17.

Figure 3:
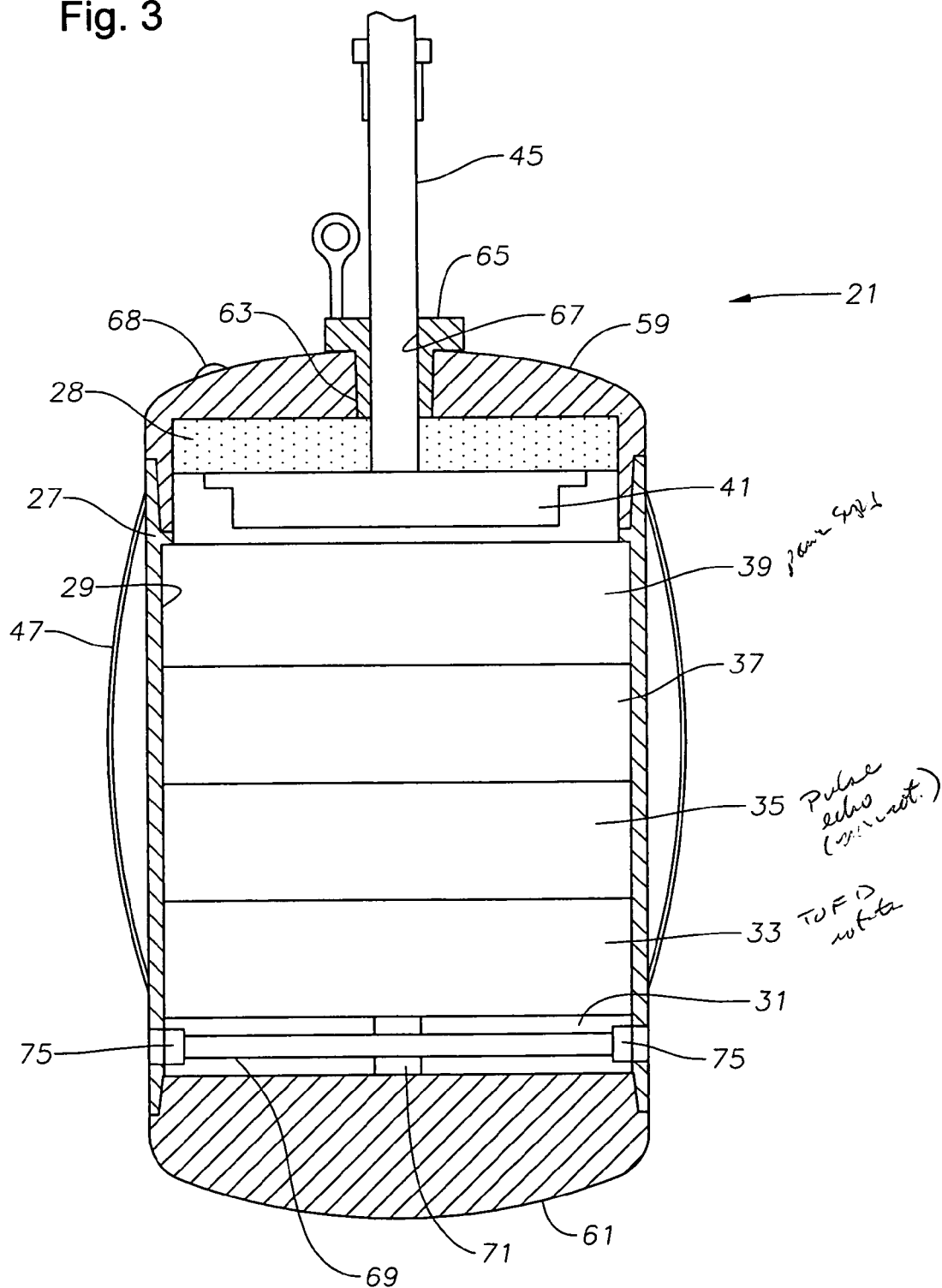
FIG. 3 is a schematic diagram of an apparatus to inspect vertically supported drilling riser pipe, according to an embodiment of the present invention.
Figure 4:
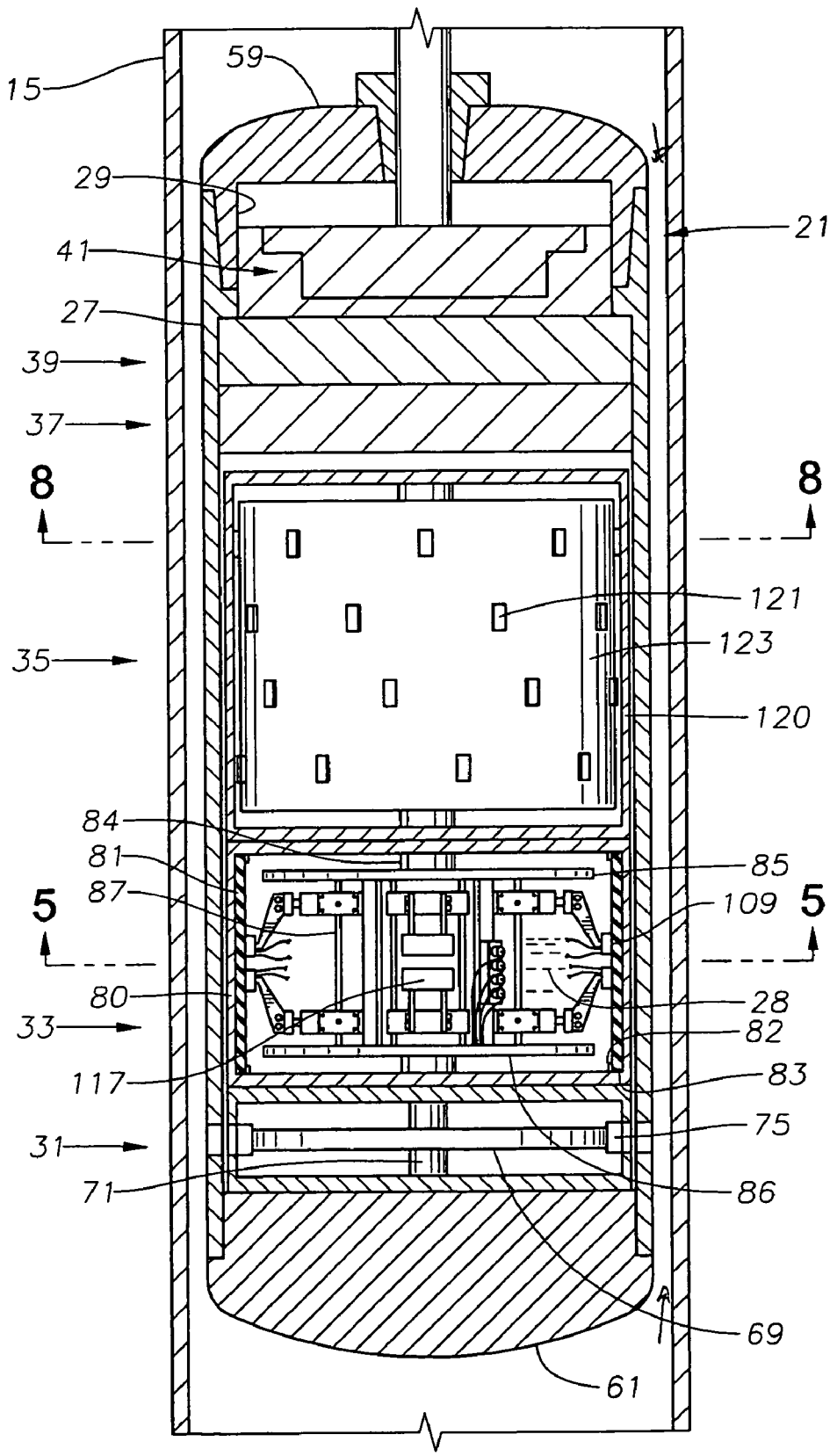
FIG. 4 is a perspective view of the inspection apparatus of FIG. 3 having portions thereof broken away for clarity, according to an embodiment of the present invention.

Referring to FIGS. 2, 3, and 4, the inspection apparatus 21 includes a tool housing having a tool housing body 27 and an inner housing chamber 29 that contains several distinct functional modules for locating and/or inspecting a riser pipe section of the deployed drilling riser pipe 15. Each module further can have its own module housing including an axially spaced apart proximal wall, distal wall, and a preferably cylindrical sidewall positioned therebetween, and an inner module chamber therewithin. Those modules preferably include a video module 31, a rotating Time of Flight Diffusion ("TOFD") module 33, a non-rotating pulse echo wall thickness module 35, a CPU/memory data convert module 37, a power supply module 39, and a wire terminal module 41. Each of the modules is positioned within the inner housing chamber 29 and is preferably independently sealed from the others and can include provisions for pressure equalization either internally or through venting through preferably filtered vent apertures (not shown). A centralizer 47, preferably in the form of a plurality of bow springs, engages the inner diameter of the drilling riser pipe 15 in order to maintain the inspection apparatus 21 aligned within the drilling riser pipe 15 during deployment and extraction and to prevent the inspection apparatus 21 from rotating. The centralizer 47 allows the tool housing body 27 to have a smaller outer diameter. For example, on a twenty-one inch riser pipe, the outer diameter can be ideally selected to be approximately twelve inches.

In the preferred embodiment of the present invention, the inspection apparatus 21 can further be described as truly modular in nature such that the inspection apparatus 21 need only be selectively loaded with module components (tools) required for an individual user's (customer's) desired application. The housings of each of the modules 31, 33, 35, 37, 39, 41, contain the various electronics and other equipment required to perform the testing.

Referring to FIGS. 2 and 3, the operational portion of the inspection system, inspection apparatus 21, can be suspended by a primary wireline or cable 40 positioned on a wireline spool 42 which can be controlled by an operator having access to a preferably surface-based controller 43. The primary wireline or cable 40 and control thereof is well known to those skilled in the art and thus, will not be described in detail. Controller 43 may be a personal or laptop computer connected to a data converter 44 or an automatic on-board controller positioned in the CPU/memory data convert module 37. Regardless of the location, controller 43 can command the extension and retraction of the inspection apparatus 21 down through a bore 23 of the deployed drilling riser pipe 15 in order to collect data regarding the status of the drilling riser pipe 15. Data can be compiled and stored in the CPU/memory data convert module 37 for later downloading or can be transmitted directly to the surface controller 43 via an umbilical cord 45 deployed from an umbilical cord spool 49, with power to the apparatus 21 preferably being supplied through the umbilical cord 45 via a power converter 55. The centralizer 47, described in further detail later, maintains the inspection apparatus 21 aligned within the drilling riser pipe 15 during deployment and extraction. Note, the primary wireline or cable 40 is also preferably collected and stored on the wireline spool 42 similar to that of the umbilical cord spool 49, and thus, the following discussion regarding the umbilical cord spool 49 can apply equally to the primary wireline spool 42.

In an embodiment of the present invention, the spool 49 can be associated with a cable length tracker 51 that tracks the amount of umbilical cord 45 or wireline 40 deployed in order to provide the operator with an indication of the vertical distance that the inspection apparatus 21 is located from a zero point at the top end of the drilling riser pipe 15 or other selected reference point. The cable length tracker 51 is mounted adjacent a deployment section of the spool 49 to provide the relative position of the inspection apparatus 21 with respect to its location within the drilling riser pipe 15. The cable length tracker 51 is known to those skilled in the art and can be, for example, a conventional odometer-type unit that uses a light beam that passes through a number of apertures (not shown) formed in a disc (not shown), the disc rotating responsive to the deployment of the umbilical cord 45 or wireline. The disc freewheels and thus is not subject to cable slippage that would erroneously affect the odometer information provided to the operator.

In an alternate embodiment of the present invention, the primary wireline or cable 40 has one or more electrical conductors, and thus can be provided to not only deploy or retrieve the apparatus 21, but also to provide for the transmission of control signals, the receipt of data signals, and the transmission of electrical power. In this alternate embodiment, the cable length tracker 51 is associated with wireline 40 rather than umbilical cord 45, the separate umbilical cord 45 not being necessary. In still another embodiment of the present invention, the inspection system includes an emergency recovery system that can allow recovery of the apparatus 21 in the event of a breakage of the primary wireline 40. The emergency recovery system is preferably in the form of a secondary wireline or cable (not shown) positioned within the umbilical cord 45.

Figure 7:
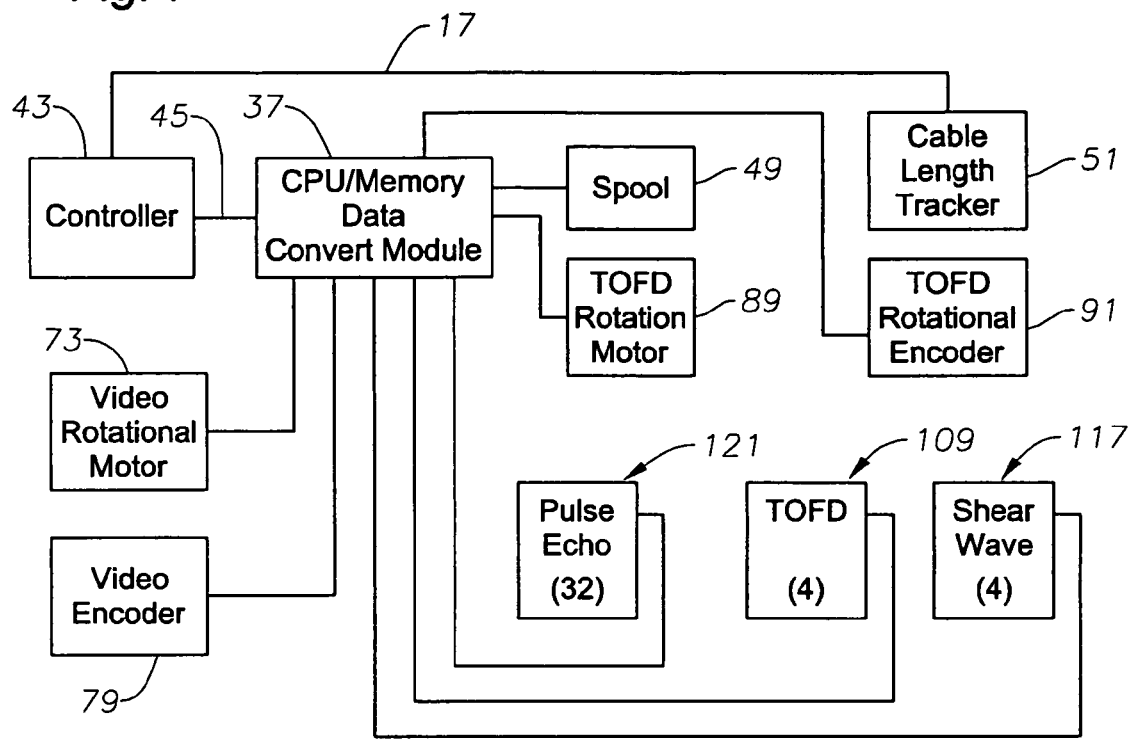
FIG. 7 is a schematic illustration of the various components of the inspection system of FIG. 2, according to an embodiment of the present invention.

Referring to FIGS. 2 and 7, the controller 43, preferably in the form of a surface-based controller, can remotely control the inspection apparatus 21 through the umbilical cord 45, which includes power/control lines, therein. The controller 43 includes a power supply/converter (not shown) and standard computer components such as a monitor, a keyboard, and a joystick. The controller 43 accepts input from the CPU/memory data convert module 37, through conductors in the umbilical cord 45 and data converter 44 to record and store data and imagery of the deployed drilling riser pipe 15. Controller 43 also accepts input from the cable length tracker 51 to control the deployment of the inspection apparatus 21. The controller 43 can control the deployment and retraction rate of the inspection apparatus 21 through the spool 49 using feedback from the cable length tracker 51.

Control signals are also sent by the controller 43 through the CPU/memory data convert module 37 to provide instructions and control to the non-rotatable pulse-echo wall thickness module 35, the rotating TOFD module 33, and the video module 31. The controller 43 can allow the operator to utilize the video module 31 to search for welds 52 or examine the inner diameter of the drilling riser pipe 15 for corrosion or obstructions, and can allow the operator to command the TOFD module 33 to perform the TOFD and/or shear wave inspection on a located weld 52. Advantageously, the video module 31, rotatable TOFD module 33, and non-rotatable pulse-echo wall thickness module 35 can each be controlled independently. The CPU/memory data convert module 37 can, in real-time, provide the controller 43 with return data collected by the non-rotatable pulse-echo wall thickness module 35, the rotating TOFD module 33, and the video module 31, or can store part or all of the data for later download. Advantageously, the CPU/memory data convert module 37 can include or interface with sound filters (not shown) so that only the desired sound energy will be received or returned.

Many of the functions of the controller 43 can be implemented in the CPU/memory data convert module 37 and thus, the inspection apparatus 21 can run fully automated, gathering data for later download. The non-rotating pulse echo module 35 or a separate pulse echo module (not shown) preferably adjacent the video module 31 can be used for detecting and storing the location of the welds 52. Having located the welds, the controller 43 can position the video camera module 31 adjacent the weld 52 to selectively record the appearance of the weld 52 to be inspected by the TOFD module 33, and can position the TOFD module 33 adjacent the weld to perform the weld volume and/or weld root inspection. Alternatively, the controller 43 or CPU/memory data convert module 37 can be preprogrammed to allow for data acquisition at pre-programmed points without the need for the apparatus 21 to necessarily stop its vertical decent or recovery, depending upon the modular configuration of the apparatus 21.

The controller 43 and/or the CPU/memory data convert module 37 can also monitor and control internal pressure, if necessary, depending upon whether the modules are vented or whether the modules are provided with internal pressurization equalization. This allows the apparatus 21 to achieve depths as deep as 10,000 feet below sealevel.

Referring to FIG. 3, the wire terminal module 41, also positioned within the inner chamber 29 of housing 27, provides an electrical power and/or data connection between the controller 43 and support modules 37, 39, and operational modules 31, 33, 35, according to a method as known and understood by those skilled in the art.

The power supply module 39 of the inspection apparatus 21 is also positioned within the inner chamber 29 of housing 27. The power supply module 39 performs power conversion of the external power supplied through the umbilical cord 45 and provides conditioned power to the various modules of the inspection apparatus 21. Alternatively, the power supply module 39 can contain either a primary or backup power source to independently power the inspection apparatus 21.

The centralizer 47 is primarily positioned external to the outer surface of the housing 27 and is adapted to maintain the operational portion of the inspection apparatus 21 aligned within the drilling riser pipe 15. The centralizer 47 aids in stabilizing the inspection apparatus 21. In one embodiment of the present invention, the centralizer 47 includes a plurality of spring bands connected to the external surface of the housing 27, as illustrated. In a second embodiment of the present invention, the centralizer 47 is in the form of a plurality of wheels (not shown) spring biased outwardly away from and perpendicular to the housing 27 and correspondingly perpendicular to the inner diameter of the drilling riser pipe 15. Either of these embodiments provide the inspection apparatus 21 the ability to substantially maintain longitudinal alignment with the longitudinal axis of the drilling riser pipe 15 while passing over imperfections on the inner diameter of the drilling riser pipe 15. The centralizer 47 also can provide sufficient friction with the inner diameter of the drilling riser pipe 15 to prevent unwanted rotation caused by the torque or inertia resulting from a rotation of the rotatable TOFD module 33.

Referring to FIGS. 3 and 4, as noted above, the inspection apparatus 21 is a relatively self-contained unit. The tool housing body 27 preferably surrounds an inner housing chamber 29 that encloses the several module sections. The tool housing body 27 is capped at a proximal end by a proximal housing cap 59 and capped at a distal end by a distal housing cap 61. The proximal housing cap 59 and distal housing cap 61 are preferably threadingly engaged with and sealed to the inner circumference of the proximal and distal ends of the housing body 27. Alternatively, the caps 59, 61, may be threaded to an external portion of the proximal end of the housing body 27, welded on either internal or external portions, or attached by other means as known and understood by those skilled in the art. The proximal housing cap 59 includes an opening 63 which allows the umbilical cord 45 to transit between the wire terminal module 39 and the external environment. A primary seal 65 includes an umbilical cord conduit 67 that sealingly surrounds the umbilical cord 45 at opening 63. The primary seal 65 is preferably of the type that can be threaded into opening 63 in the proximal housing cap 59 but can be connected by other means known to those skilled in the art. Note, although the tool housing body 27 can be in the form of a frame structure rather than a solid body, as illustrated in FIG. 3, providing the tool housing body 27 in the form of a solid body is preferred as there could be residual debris remaining in the deployed riser pipe 15.

The tool housing body 27 is preferably vented with seawater 28 to remove air and allow pressure equalization between the inner diameter of the tool housing body 27 and outer diameter of each of the modules. Correspondingly, each of the modules positioned within the tool housing body 27 are further preferably vented within the inner housing chamber 29, to allow for the removal of air and to provide for pressure equalization between the outer surface of each module and inner module chamber of each module. In an alternative embodiment of the present invention, instead of venting the tool housing and each of the modules, the umbilical cord 45 can include a pressure line (not shown), therewithin. A pressure sensor, preferably in the form of a pressure transducer 68 and preferably connected to the proximal housing cap 59, can transmit a signal back to the controller 43. A pressure pump (not shown), responsive to either the controller 43 or the CPU/data convert module 37, can then provide pressurized fluid through the pressure line in the umbilical cord 45 to substantially equalize the internal pressure of the tool housing body 27 and internal pressure of each of the modules within the tool housing body 27 to preferably that of the hydrostatic pressure associated with that encountered by the pressure transducer 68. Regardless of the configuration, the electronic components within the CPU/memory data convert module 37, power supply module 39, and wire terminal module 41 are sealed with a sealed means known and understood by those skilled in the art to prevent corrosion.

Referring to FIGS. 3 and 4, in the illustrated embodiment, the inspection apparatus 21 includes a video module 31, a rotating TOFD module 33, a non-rotating pulse echo wall thickness module 35, a CPU/memory data convert module 37, a power supply module 39, a wire terminal module 41, and a centralizer 47. The video module 31 is positioned within the inner housing chamber 29, preferably adjacent the distal end of the tool housing body 27, and is positioned to view an inner diameter of the drilling riser pipe 15. The housing body 27 adjacent the video module 31 is preferably substantially transparent around its entire circumference to provide for visual viewing from within the video module 31. The video module 31 includes a rotational arm or plate 69 that is mounted to a video module drive shaft 71 driven by a video module rotational motor 73 (FIG. 7). A pair of video cameras 75 are preferably mounted to the rotational arm or plate 69 to provide independent positioning of the video cameras 75 in order to provide a visual inspection and recording of the inner diameter of the drilling riser pipe 15 and to detect a position of a weld 52. Alternatively, the video camera or cameras 75 can include lenses such as wide-angle lenses (not shown) and can be fixedly mounted to view the inner diameter of the drilling riser pipe 15 from a single fixed position. This feature is available because the inspection apparatus 21 can be maintained approximately in the center of the bore 23 (FIG. 1) of the drilling riser pipe 15. A video encoder 79 (FIG. 7) provides the azimuth information to the controller 43 if being controlled by an operator or to the CPU/data convert module 37 if functioning in a preprogrammed or automated mode.

Referring to FIGS. 3 and 4, the rotating TOFD module 33 of the inspection apparatus 21 can also be positioned within the inner housing chamber 29. The rotating TOFD module 33 includes a TOFD housing 80 having an inner chamber containing the TOFD modular components. The TOFD modular components include a fluid carrier 81 positioned to line at least a portion of the inner diameter (inner surface peripheries) of the housing 80. The fluid carrier 81 is preferably in the form of a flexible bladder filled with fluid to insure that there are no air gaps which would cause disruption of the sound signal. A mounting apparatus known and understood by those skilled in the art, such as, for example, a pair of annular snap rings 82 holds the fluid carrier 81 in the selected location. A pair of o-rings 83 positioned adjacent proximal and distal sides of the fluid carrier 81 seal the fluid carrier 81 into TOFD module housing 80. The inner chamber of the TOFD housing 80 contains a fluid such as seawater 28 in a configuration where the modules are vented or an acoustic fluid in a configuration where the modules are sealed. The inner chamber of the housing body 27 also contains a fluid such as seawater 28 in a configuration where the housing body 27 is vented or an acoustic fluid in a configuration where the housing body 27 is sealed. The fluid can form a liquid coupling which provides for the transmission of soundwaves (described later) from within the TOFD module 33 and to the drilling riser pipe 15.

Included within the module also is a TOFD drive shaft 84 which extends parallel to the longitudinal axis L of the housing 15, and proximal and distal support plates 85, 86, positioned parallel to each other and mounted to the TOFD drive shaft 84. A plurality of support rods 87 extend between the proximal and distal support plates 85, 86, and are parallel to each other and parallel to the axis of drive shaft 84. A TOFD module rotational motor 89 (FIG. 7) is further connected to the drive shaft 84. The TOFD module rotational motor 89 has a linkage (not shown) that allows it to rotate the drive shaft 84 in an increment that preferably is no more than one revolution, preferably either 90 or 180 degrees, then rotate back the other direction.

The TOFD module 33 can perform an inspection on a first weld 52 by rotating the module 33 either clockwise or counterclockwise for the selected degrees of rotation, and can perform an inspection on a second weld 52 by rotating in an opposite direction for the selected degrees of rotation. A rotational encoder 91 (FIG. 7) provides an azimuth indication of the precise angle of rotation of drive shaft 84 to the operator through the CPU/memory data convert module 37 if being manipulated "real-time" and/or to the CPU/memory data convert module 37 for independent control if being deployed in a preprogrammed automatic run sequence.

A plurality of transducer mounting blocks 93 (FIG. 6) are mounted to a supporting structure such as support rods 87 or alternatively directly to one of the support plates 85, 86. When configured to mount to support rods 87, the transducer mounting blocks 93 can be positioned at preselected points along the lengths of support rods 87, which preferably extend through holes within them. The longitudinal locations for positioning the mounting blocks 93 can be selected dependent upon the approximate longitudinal length of the welds 52 to be inspected.

Figure 6:
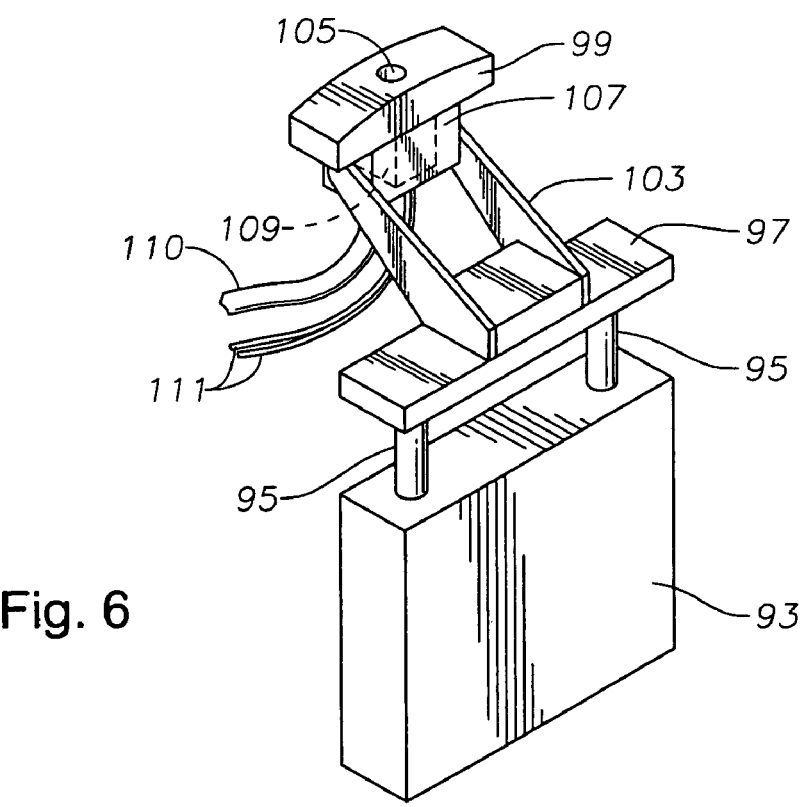
FIG. 6 is a perspective view of one of the transducer assemblies of the inspection apparatus of FIG. 4, according to an embodiment of the present invention.

Referring to FIG. 6, each transducer mounting block 93 can also include a pair of supporting rods 95 which are preferably fixedly located at a predetermined radial position commensurate with the inner diameter of the TOFD module housing 80 and thickness of fluid carrier 81. The plurality of supporting rods 95, alternatively, can be in the form of adjustable extensions including appropriate mechanical linkage for prepositioning the supporting rods 95 radially inward and outward between retracted and extended positions. A transducer plate 97 is mounted to the outer ends of the support rods 95 for carrying a transducer shoe 99. The transducer shoe 99 can be a hard plastic material and, in an embodiment of the present invention, can be readily replaced for different inner diameters of TOFD module housing 80.

The TOFD module housing 80 (FIG. 4) is selected based on the inner diameter of tool housing 27, which can be further selected based on the inner diameter of the drilling riser pipe 15. The transducer shoe 99 can be connected to the transducer plate 97 by a means known by those skilled in the art. In an embodiment of the present invention, a pair of braces 103 can be used. The braces 103 can extend outward from drive shaft 84 and are preferably angled relative to the longitudinal axis L of the housing 27.

Figure 5:
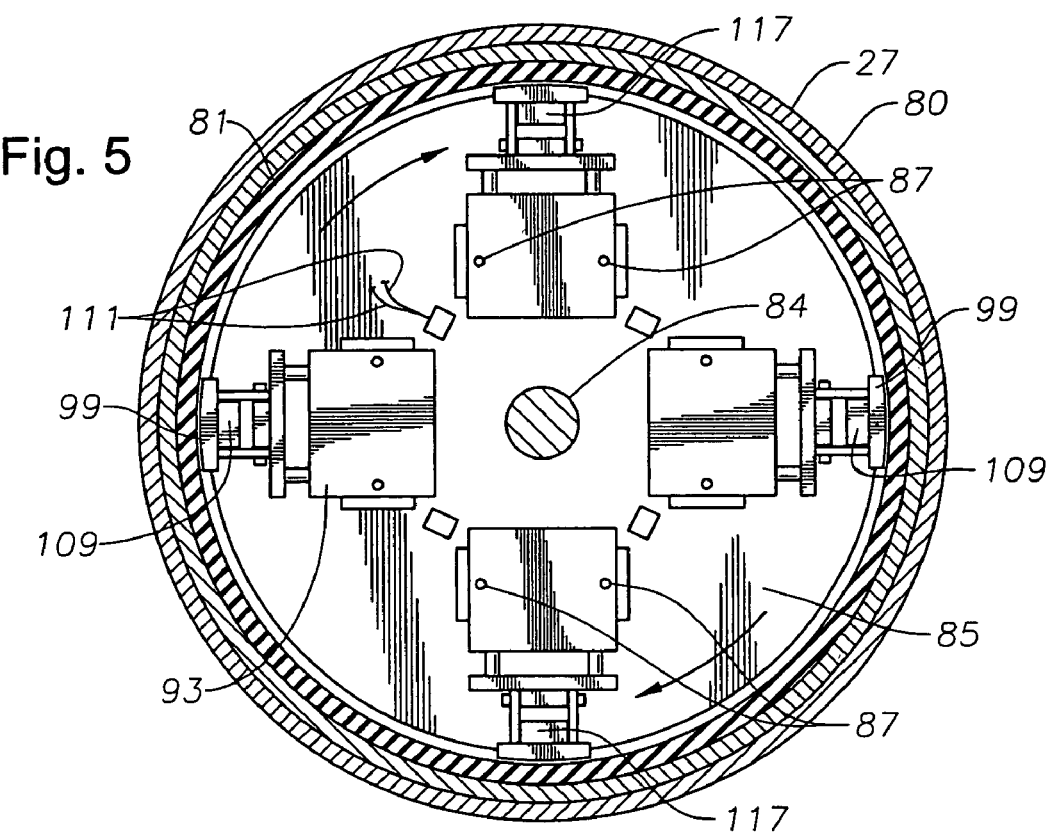
FIG. 5 is a cross-sectional view of the inspection apparatus taken along the 5—5 line of FIG. 4, according to an embodiment of the present invention.

Referring to FIGS. 5 and 6, each transducer shoe 99 has an outer face that can curve in a convex form for rotationally mating with the inner diameter of the fluid carrier 81, which is, inturn, fixedly positioned in contact with inner surface peripheries of the TOFD housing 80, which is further fixedly positioned with respect to tool housing body 27. The TOFD rotational motor 89 (FIG. 7) can drive the drive shaft 84 which causes each transducer shoe 99 to rotate relative to, and in contact with, the fluid carrier 81. The fluid carrier 81 insures that there is no airgap between the TOFD housing 80 and the transducer shoe 99. Any air trapped between the TOFD housing 80 and tool body housing 27 should be purged through venting, if so configured. Whether or not so configured, any trapped air should gravitate away from the inner portion of the tool housing 27 adjacent the TOFD module 33 and wall thickness module 35 and toward the proximal end of tool housing body 27 due to the vertical deployment. The centralizers 47 (FIG. 1) prevent rotation between the tool housing body 27 and the riser pipe 15, thus, resulting in a relative rotation between the riser pipe 15 and the transducers 93. This relative rotation allows for the TOFD inspection, described later.

Referring to FIG. 6, in an embodiment of the present invention, a recess or cavity 105 can extend from the outer face of each transducer shoe 99 inward through transducer shoe 99 and transducer housing 107. A transducer 109 is mounted preferably to the inward side of upper spacer block 107 at the base of recess 105. The transducer 109 can be a conventional piezoelectric device that will emit and/or receive acoustical signals. A small flexible tube 110 can join a fluid passage (not shown) in each transducer housing 107 for delivering fluid to the recess 105 to ensure there are no air gaps between transducer 109 and the inner diameter of the fluid carrier 81, which would cause a loss of acoustic signal. Tube 110 and can also serve provided fluid to aid in pressure equalization. In a configuration where the TOFD module 33 is vented to the ambient seawater 28, fluid supplied by the small flexible tube 110 can further help minimize risk of debris contamination within the module inner chamber. A fluid supply line (not shown) within the umbilical cord 45 can provide such fluid to the tube 110. In the preferred embodiment, each transducer shoe 99 has only one transducer 109. Conductors, such as the pair of wires 111, illustrated, lead to the transducer 109 to supply electrical energy to cause a sound pulse to be emitted or to receive a sound pulse converted to electrical energy. The type of transducer used for pulse echo measurements convert acoustical reflected signals received into electrical energy, which is transmitted through the wires or other forms of conductors to the CPU/memory data convert module 37.

Referring to FIG. 4, the rotating TOFD module 33 preferably also has two TOFD transducer pairs adapted to inspect for and obtain data on weld volume defects by the TOFD method, one transducer 109 of each pair of transducers acting as a transmitter and the other transducer 109 of the each pair of transducers acting as a receiver. The TOFD transducers 109 within each pair are spaced axially apart a selected distance along the longitudinal axis L of the housing 27, with one TOFD transducer 109 being more forward of the other. Each pair of TOFD transducers 109 is 180 degrees from the other pair of transducers. The forward transducer 109 in each pair is located in the same radial plane as the forward transducer 109 in the other pair. Similarly, the rearward transducer 109 in each pair is located at the same axial position along the longitudinal axis L of the housing 27 of the inspection apparatus 21 as the rearward transducer 109 of the pair located 180 degrees away. Though only one pair of TOFD transducers 109 is required, one adjacent and axially forward of the other, the implementation of two pairs lessens the requirement of rotation to that of 180 degrees. Alternatively, four pair of TOFD transducers 109 would reduce this requirement to that of 90 degrees. Note, a different number of transducer pairs along with a different number of associated mounts can alternatively be utilized.

Figure 9:
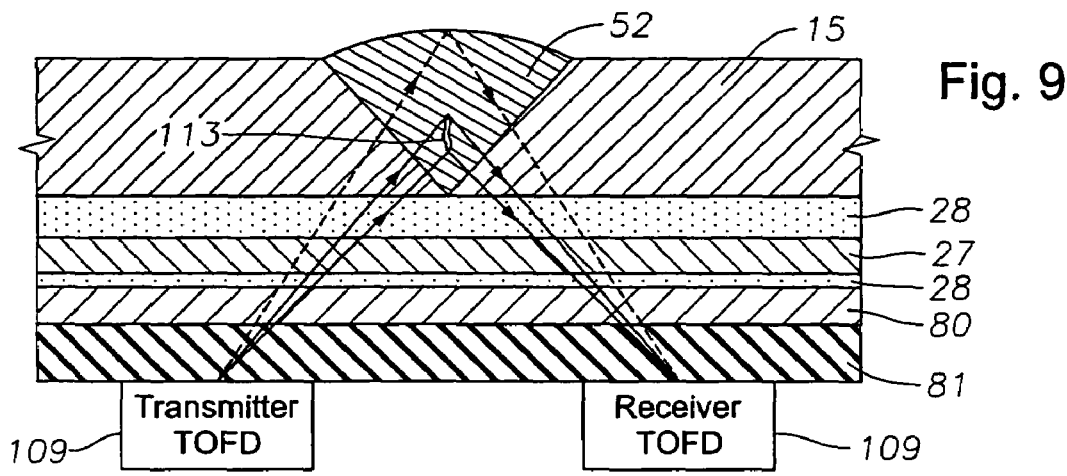
FIG. 9 is a schematic cross-sectional view of a weld of the drilling riser of FIG. 1, showing TOFD transducers inspecting for defects in the volume of the weld, according to an embodiment of the present invention.

Referring to FIG. 9, shown is the TOFD method. As stated above, within each pair of the TOFD transducers 109, one of the TOFD transducers 109 is a transmitter and the other is a receiver, with the receiver spaced axially from the transmitter. The TOFD transducers 109 are positioned by or through the use of the controller 43 on both sides of and in close proximity to a weld 52. The weld 52 is a typical weld formed between two beveled ends of tubular members that make up a section of the drilling riser pipe 15. The weld 52 typically has a triangular cross-section, with the apex or root of weld 52 being at the inner diameter of the section of the drilling riser pipe 15 and the weld cap at the outer diameter of the section of the drilling riser pipe 15. The axial distance between the TOFD transducers 109 in each pair of TOFD transducers is greater than the width of the cap of weld 52. The TOFD transducers 109 are preferably angled toward each other so that the signal from the transmitter TOFD transducer 109 passes through the wall of the drilling riser section being inspected at a selected angle, such as, for example, about 60 degrees and reflects ultrasonic energy (sound waves) to the receiver TOFD transducer 109.

The TOFD transducers 109 are rotated by the TOFD module rotational motor 89 (FIG. 7) the predetermined angular distance about the TOFD drive shaft 84 (FIG. 4) while the transmitter TOFD transducer 109 emits sound pulses. The sound pulses (acoustic signals) pass through any acoustic fluid, e.g., seawater 28, between transducer 109 and fluid carrier 81, through fluid carrier 81, through the TOFD module housing 80, through any acoustic fluid between the TOFD module housing 80 and the tool housing body 27, through the tool housing body 27, through the ambient seawater 28, through the drilling riser pipe 15, and through the volume of the weld 52. If there is no flaw 113 in the weld, the signal will reflect off the outer diameter of the weld 52 and return back to the receiver TOFD transducer 109. If the weld 52 has a flaw 113, some of the signal will be diffracted at the tips of the flaw 113. The diffracted acoustic signals are then also received by the receiver TOFD transducer 109, as illustrated. The time that it takes for the sound waves to reach receiver TOFD transducer 109 is different for the diffracted pattern caused by the flaw 113 versus the non-diffracted pattern. This difference is analyzed in a manner known by those skilled in the art to provide an indication of the flaw 113. This described TOFD method measures the volume of the weld 52, which includes substantially all of the weld 52 except for the root portion adjacent of the inner diameter of the drilling riser pipe 15. The TOFD inspection methodology is very capable of determining defects for the volume of weld 52 but lacks capability for properly inspecting the root of weld 52.

Figure 10:
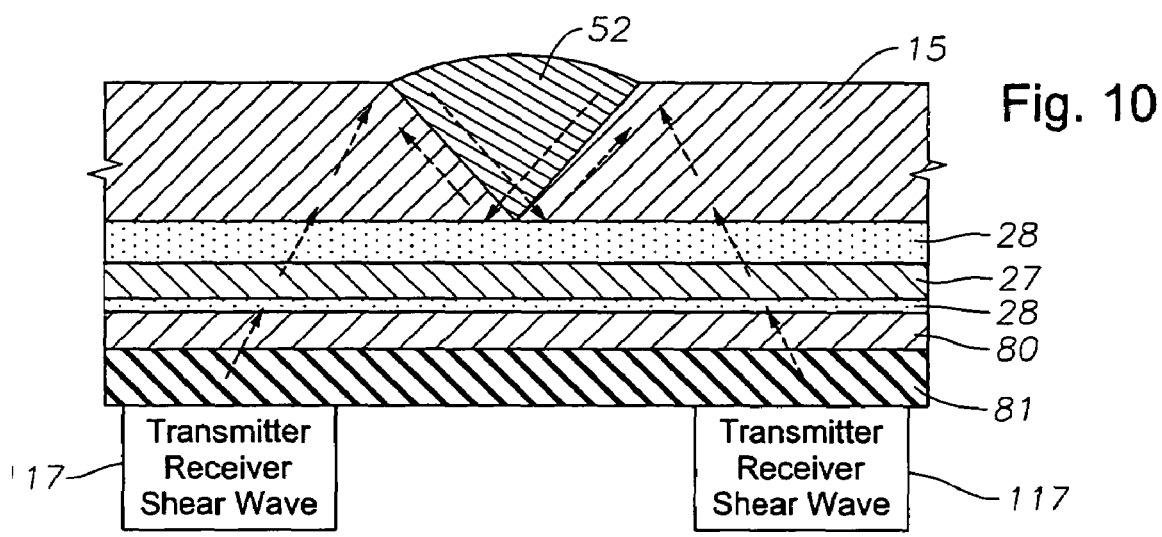
FIG. 10 is a schematic cross-sectional view of the weld of FIG. 8, showing pulse echo shear wave transducers inspecting for defects in the root of the weld, according to an embodiment of the present invention.

Referring to FIG. 10, in an embodiment of the present invention, the inspection apparatus 21 also has two shear wave transducer pairs (FIGS. 4 and 5) adapted to inspect for and obtain data on weld root defects by pulse echo shear wave techniques. Each shear wave transducer 117 of a pair can be spaced a selected axial distance from the other transducers 117 of the pair, and each pair of transducers 117 can be positioned approximately the same axial distance as the forward and rearward TOFD transducers 109. The pairs of shear wave transducers can be also located 180 degrees apart from each other. One of the shear wave transducers 117 of the each pair of transducers is positioned to transmit an acoustic signal to the other shear wave transducer 117 of the pair and to receive an acoustic signal on a different frequency from the other shear wave transducer 117. The other shear wave transducer 117 of the pair of shear wave transducers also functions accordingly. In an embodiment of the present invention, the pair of TOFD transducers 109 is located at the zero degree position and another pair at the 180 degree positions, while shear wave transducers 117 are located at the 90 degree and 270 degree positions.

The pulse echo shear wave technique can be employed, as illustrated in FIG. 10, to inspect for any flaws in the root portion of weld 52. Each shear wave transducer 117 is preferably of a pulse echo type, having both a receiver and a transmitter, and can be angled toward the other in a manner similar to TOFD transducers 109 (FIG. 9). The shear wave transducers 117 are also axially spaced apart along the longitudinal axis of housing 27 for positioning on opposite sides of weld 52 at a spacing similar to that of the TOFD transducers 109. Each shear wave transducer 117 within each pair emits a sound pulse, but at a slightly different time from the other transducer 117 in the same pair so as to avoid interference with each other. The shear wave transducers 117 are oriented so that the sound waves are directed toward the outer diameter of the section of the drilling riser pipe 15 near but not through the volume of weld 52. The angles are selected so that the sound pulse will contact the outer diameter of the drilling riser pipe 15 and reflect back through the root of weld 52. Functionally, if the root is free of any defects, the reflected signal contacts the inner diameter of the section of the drilling riser pipe 15 between shear wave transducers 117 and reflects back outward. Because of the positioning of the shear wave transducers 117, the shear wave transducers 117 should not receive any reflected signals if the root is free of defects. However, if a flaw is encountered, diffraction will occur, and one or both of the shear wave transducers 117 in each pair will receive a return signal that emanated from the other shear wave transducer 117. The controller 43 analyzes the return signal in a known manner to provide an indication to the operator.

Ultrasonic transducer signals (acoustic signals) are sent from within the portion of the housing 27 surrounding the rotating TOFD module 33 without either transducer 109, 117, having to make contact with the body of the drilling riser pipe 15. This is accomplished by flooding the inner diameter of the drilling riser pipe 15 with seawater 28 or some other acoustic liquid fluid in order to act as a medium or liquid coupling for carrying sound energy from the apparatus 21 to the body of the drilling riser pipe 15. Additionally, the venting of the tool housing body 27 and TOFD module 33 with either seawater or supplying it with some other liquid coupling fluid allows for transport of the signal from within the inner chamber 29 of the inspection apparatus 21. As described above with respect to the TOFD transducers 109, whether the transducers 109, 117, are used for weld root or weld volume inspection, through use of an acoustic fluid such as seawater 28, the ultrasonic transducer signals can pass from the transducers 109, 117, through the acoustic fluid forming a liquid coupling, through the fluid carrier 81, through the TOFD module housing 80, through any acoustic fluid filling any gap between the outer diameter of the TOFD module housing 80 and inner diameter of the tool housing body 27, through the tool housing body 27, through the ambient seawater 28 (forming a liquid coupling), through the drilling riser pipe 15 adjacent the weld 52, and finally through the weld 52. Note, maintaining a liquid coupling in contact with both the drilling riser pipe 15 and transducers 109, 117, is an important feature used to ensure proper operation of the TOFD module 33. If any air is present, the acoustic signal may be lost.

Figure 8:
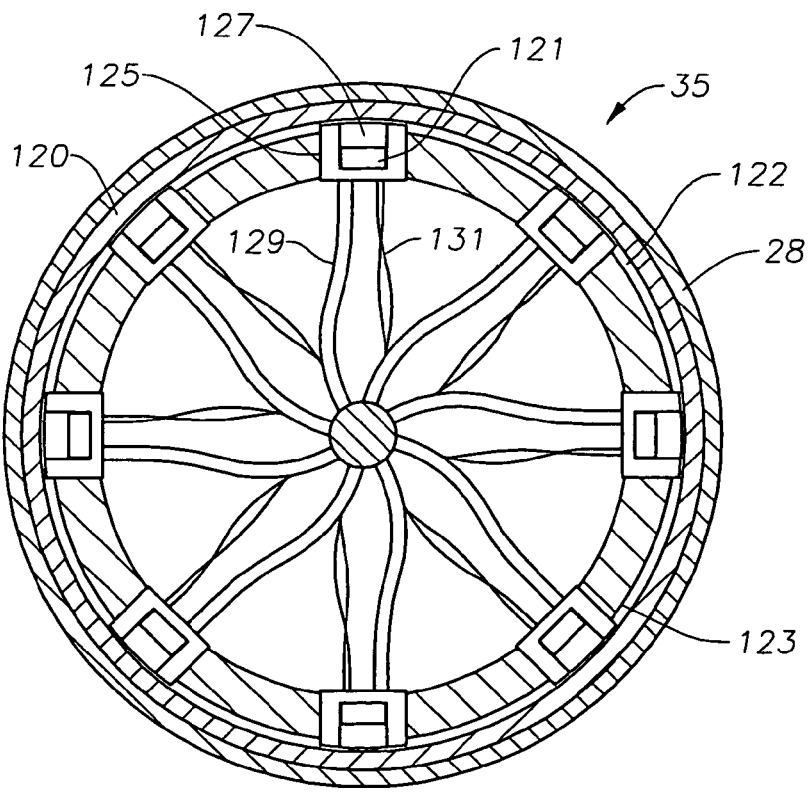
FIG. 8 is a cross-sectional view of the inspection apparatus taken along the 8—8 line of FIG. 4, according to an embodiment of the present invention.

Referring to FIGS. 3, 4 and 8, the non-rotating pulse echo wall thickness module 35 of the inspection apparatus 21 can also be positioned within the inner chamber 29 of housing 27. The non-rotating pulse echo wall thickness module 35 includes a non-rotating pulse echo wall thickness module housing 120 having an inner chamber containing a liquid coupling fluid, e.g. seawater 28, and preferably containing a 32 channel fixedly mounted transducer array that measures wall thickness utilizing pulse echo techniques. Referring primarily to FIG. 8, each transmitter/receiver pulse echo transducer 121 is of a type that transmits and receives. The 32 transmitter/receiver pulse-echo transducers 121 are positioned substantially equally spaced apart upon a preferably nonmetallic retaining ring 123, each within a separate transducer mount 125. Each transducer mount 125 includes a recess 127 extending from within the mount into an outer surface positioned preferably adjacent the inner diameter of the housing 120. The transmitter/receiver pulse echo transducer 121 is located adjacent the base of the recess 127. A small flexible tube 129 can join a fluid passage (not shown) in each transducer mount 125 for delivering fluid to the recess 127 to ensure there are no air gaps between each transducer 121 and the inner diameter of the module housing 120, which would cause a loss of acoustic signal and can also serve to aid in pressure equalization. In a configuration where the wall thickness module 35 is vented to the ambient seawater 28, fluid supplied by the small flexible tube 120 can further help minimize risk of debris contamination within the module inner chamber. A fluid supply line (not shown) within the umbilical cord 45 can provide such fluid to the tube 129.

Each transducer mount 125 is positioned along the inner circumference of the housing 27 surrounding the non-rotating pulse echo wall thickness module 35. The transmitter/receiver pulse echo transducers 121 are positioned such that they point radially outward, normal to the inner circumference or diameter of housing 27, and thus normal to the section of the drilling riser pipe 15 being inspected. In the exemplary embodiment, there are eight radial planes with four transmitter/receiver pulse echo transducers 121 on each plane, however, other than 32 channels and other positional combinations are within the scope of the present convention. As shown in FIG. 4, transducers 121 within each vertical plane are staggered relative to the transducers 121 in the planes above and below. Preferably, one of the transducers 121 will be located to approximately every 11.25 degrees around the circumference of housing 120.

Ultrasonic transducer signals (acoustic signals) are sent from within the housing 27 surrounding the non-rotating pulse echo wall thickness module 35 without either transducer having to make contact with the body of the drilling riser pipe 15. As with the TOFD module 33, the non-rotating pulse echo wall thickness module 35 can be either pre-filled with a liquid coupling fluid or can be vented with seawater 28 from within the drilling riser pipe 15 in order to act as a medium or liquid coupling for carrying the sound energy to the body of the drilling riser pipe 15. Preferably the housing 27 adjacent the non-rotating pulse echo wall thickness module 35 is, however, vented to the seawater 28 in the flooded body of the drilling riser pipe 15 as this provides, not only the liquid coupling, but also economically provides internal pressure equalization.

Figure 11:
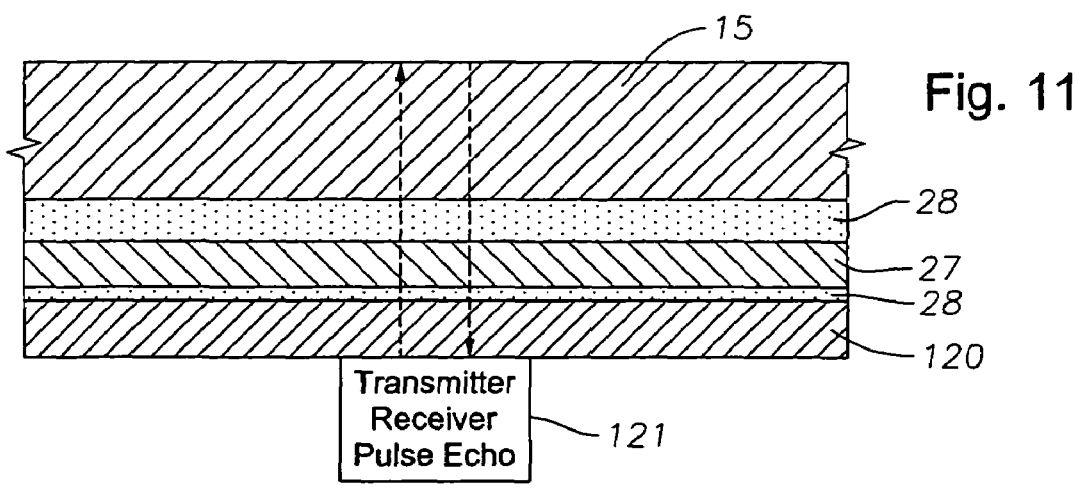
FIG. 11 is a schematic cross-sectional view of a portion of the riser in FIG. 1, showing an ultrasonic transducer measuring wall thickness utilizing a pulse echo method, according to an embodiment of the present invention.

Referring to FIGS. 8 and 11, each transmitter/receiver pulse echo transducer 121 transmits an ultrasonic (acoustic signal) through the seawater 28, which communicates to the section of the drilling riser pipe 15 being inspected. The ultrasonic transducer signal is passed from the transducers 121, through fluid forming the liquid coupling, through the wall thickness module housing 120, through any liquid coupling fluid, e.g. seawater 28, filling any gap between the outer diameter of the wall thickness module housing 120 and inner diameter of the tool housing body 27, through the tool housing body 27, through the ambient seawater 28 (forming a liquid coupling), through the drilling riser pipe 15, and to the outer diameter of drilling riser pipe 15. The signal is then reflected back to the inner diameter of the drilling riser pipe 15 and to the apparatus 21 where it is received by the reference transducer 121. The sound received by transducers 121 is converted into electrical signals, which are transmitted to the controller 43 (FIG. 2) via a pair of wires 131 connected to the CPU/data convert module 37 which, in the illustrated embodiment, is electrically connected to the controller 43 via conductors within the umbilical cord 45. The controller 43 analyzes the signals in a conventional manner. The thickness of the section of the drilling riser pipe 15 being inspected is determined by measuring the time that it takes for the signal to return to the inner diameter of the section of the drilling riser pipe 15.

Referring to FIG. 2, the non-rotating pulse-echo wall thickness module 35 utilizes a separate channel for each transmitter/receiver pulse echo transducer. With 32 channels, no rotation is required for a substantially full 360 degrees scan, because transducers 121 (FIG. 4) are located approximately every 11.25 degrees. Because the inspection apparatus 21 need not be stopped to monitor wall thickness, in the illustrated configuration, an entirely automated system for measuring such wall thickness can be employed. Advantageously, the umbilical cord 45 would not be necessary where the inspection apparatus 21 functions entirely automated. Note that a different number of transducers than 32 could be utilized to improve or reduce coverage or redundancy. Note also, this non-rotatable feature is important because having a sufficient number of transducers negates the requirement that the inspection apparatus 21 be stopped in order to inspect wall thickness/corrosion, and thus, further decreases the length of time drilling riser operations are interrupted in order to perform an inspection.

Referring to FIG. 2, advantageously, embodiments of the present invention include methods of inspecting a vertically supported drilling riser pipe 15. In operation, the operator can inspect the wall thickness and the status of the welds 52 of the drilling riser pipe 15 during one round trip pass down and back up through the deployed drilling riser pipe 15. The inspection apparatus 21 does not need to be extracted from the drilling riser pipe 15 between inspecting for corrosion with pulse echo transducers 121 and inspecting for weld defects with TOFD transducers 109 and/or the shear wave transducers 117. The operator can take drilling riser pipe readings and inspect for corrosion on the trip down to the lowest portion of the drilling riser pipe 15 to be inspected, and take weld readings on the way back up. This could, however, be reversed. Also, if desired, the operator could inspect the drilling riser pipe 15 for corrosion and inspect the welds 52 as they are encountered. Additionally, the inspection apparatus 21 can be pre-programmed by the operator to automatically perform the inspection without additional operator control.

Referring to FIGS. 1 and 2, in the preferred technique, the operator first disconnects a lower marine riser package 26 (FIG. 1) of the drilling riser from a blowout preventer 19. The operator then flushes an inner diameter of the drilling riser pipe 15 with a cleansing fluid such as, for example, seawater 28. Though not necessarily required for an electronic inspection, where video devices are to be used, the cleansing provides for an improved image of the inner diameter of the drilling riser pipe 15 to the operator. Additionally, the cleansing action can also help prevent erroneous readings due to contaminants remaining along the inner diameter of a section of the drilling riser pipe 15 to be inspected. The operator connects the inspection apparatus 21 to wireline deployment spool 42 for deployment via wireline and functionally connects umbilical cord 45, generally housed on an umbilical cord spool 49, to the controller 43. Alternatively, the CPU/memory data convert module 37 can be loaded with operator instructions and be battery powered so that the inspection apparatus 21 can be deployed without the need for control through the umbilical cord 45. The operator then deploys or inserts the inspection apparatus 21 into an upper end of the vertically supported drilling riser 15 through use of a diverter (not shown) on the drilling riser pipe 15 or hung off a spider 17.

Referring to FIGS. 2, and 4, the inspection apparatus 21, provided by the operator, can include a plurality of the fixedly mounted ultrasonic wall inspection transducers 121 for determining wall thickness of a portion of the drilling riser pipe 15. Also provided can be a plurality of the rotatably mounted weld volume inspection transducers 109, which are rotatable about a longitudinal axis L of the housing 27 of the inspection apparatus 21 for inspecting weld volume defects. The inspection apparatus 21 can also include a plurality of the rotatably mounted weld root inspection transducers 117, which generally rotate with the weld volume inspection transducers 109.

The wireline deployment spool 42 controlled by an operator through a controller 43 lowers the inspection apparatus 21 down the bore 23 of the drilling riser pipe 15 at a preselected rate and for a preselected distance. The operator then may make wall thickness tests with the wall thickness inspection transducers 121. During the descent, periodically either real-time or through pre-programming, the operator causes the wall inspection transducers 121 to emit an acoustical signal into the wall of the drilling riser pipe 15 and to detect a return acoustical signal from the wall of the drilling riser pipe 15 to determine wall thickness (FIG. 11).

The operator will normally be given instructions as to what longitudinal increments, or inspection areas, the wall thickness inspections are to be made. Also, the operator will be informed as to how many inspection sites are to be made around the inner circumference or diameter of the drilling riser pipe 15 at each inspection area or zone. In the preferred configuration, a sufficient numbers of wall inspection transducers 121 can be positioned within the inspection apparatus 21 to cover the entire 360 degrees of the inner diameter of the drilling riser pipe 15. Also, depending upon an amount of available storage capacity, preferably substantially the entire length of the drilling riser pipe 15 can be examined, thus providing as much as 100 percent coverage. Alternatively, sampling methodologies can be implemented that will identify a plurality of wall inspection sights along the drilling riser pipe 15 for collecting wall thickness data with the plurality of wall inspection transducers 121. Through use of sampling, the wall thickness transducers 121 can statistically cover a sufficient percentage of the drilling riser pipe 15 to allow less than 100 percent coverage yet still detect most, if not all, discrepancies. Regardless of the sampling methodology utilized, advantageously the wall thickness data can be collected without interrupting vertical movement of the inspection apparatus 21.

During the descent of the inspection apparatus 21, the tool housing body 27 and each of the module housings of each module can have their respective internal pressure substantially equalized to that of the hydrostatic pressure within the drilling riser pipe 15 associated with the position of the apparatus 21. Such equalization pressure is provided to prevent damage to the inspection apparatus 21 potentially associated with very high pressures which are especially profound in the lower portion of the drilling riser pipe 15. Equalization pressure can be applied within the inspection apparatus 21. For example, the tool housing body 27 and each of the modules can be pressurized by a fluid supply line (not shown) in the umbilical cord 45. In the preferred configuration, however, especially regarding those modules equipped with ultrasonic transducers, each module, along with the housing body 27, can be entirely vented in order to allow seawater 28 to equalize the pressure.

The use of the ambient seawater 28 can be advantageous because not only does such use negate the need for a fluid supply line in the umbilical cord 45, but also because the seawater 28 can act as the liquid coupling for the various transducers and can help to purge any trapped gas which may tend to disrupt proper operation of such transducers. Alternatively, rather than venting the inner chambers of the electronic support modules such as the CPU/memory data convert module 37, power supply module 39, or wire terminal module 41, each of those modules can be filled with a dielectric fluid and can include a bladder (not shown) to perform the pressure equalization function. Note, though the seawater 28 is the preferred acoustic fluid to be positioned in the drilling riser pipe 15 for inspection, other fluids such as, for example, production fluid, may function as a potential substitute where seawater is either not available or not feasible to use.

As stated above, if the wall thickness is determined during the transit of the inspection apparatus 21 down through the bore 23 of the drilling riser pipe 15, the operator then may make weld volume inspection tests with weld volume inspection transducers 121, preferably during the return transit. Rather than bringing the inspection apparatus 21 back to the top end of the drilling riser pipe 15, it is more efficient to operate the inspection apparatus 21 and perform inspections during extraction of the inspection apparatus 21, making weld inspections beginning from the far distal end of the deployed drilling riser pipe 15. Regardless of the starting point, prior to inspecting the plurality of welds 52 with the weld volume inspection transducers 109 and weld root (shear wave) inspection transducers 117, if so installed, the location of the first weld inspection site should be determined. If video cameras 75 or some form of weld detection sensors are installed, the operator can either manually or through automated systems detect and store the location of the weld inspection site in the weld inspection area either on the transit down or on the transit back up. This is accomplished with the use of cable length tracker 51 associated with either the wireline spool 42 or umbilical cord spool 49.

After the inspection apparatus 21 has determined a weld inspection site of a weld inspection area, the operator can, through the controller 43, position the inspection apparatus 21 in a position at the weld inspection site that places a first and a second weld volume inspection transducer 109 on opposite sides of a weld 52. The operator then temporarily stops vertical or longitudinal movement and then simultaneously rotates the first and the second weld inspection transducers 109 along the circumference of the inner diameter of the drilling riser pipe 15 at the inspection site. As stated above, this rotation is preferably within a fluid carrier 81. The fluid carrier 81, which is also generally in contact with transducers shoes 99, ensures a proper acoustic coupling between the weld volume inspection transducers 109 and weld root inspection transducers 117 and the inner TOFD module housing 80. The exterior surface of the tool housing body 27 is surrounded by seawater 28 to further provide the acoustic coupling between the transducers 109, 117, and the inner diameter of the drilling riser pipe 15.

Referring to FIGS. 9 and 10, the operator causes the first weld volume inspection transducer 109 to emit an acoustical signal into the weld 52 and the second weld volume inspection transducer 109 to receive a return acoustical signal, to determine if a volume of the weld 52 has any defects. Additionally, the operator can simultaneously position a first and a second weld root inspection transducer 117 on opposite sides of the weld 52 along with the first and the second weld volume transducers 109. The operator can cause the first weld root transducer 117 to emit an acoustical signal and can enable the second weld root transducer 117 to receive an acoustical signal from a root of the weld 52 to determine if the root of the weld 52 has any defects.

After determining the position of a first weld 52, the operator will have a general indication of the position of the next weld 52 based on the location of the prior weld 52 inspected because the approximate spacing of the welds 52 are generally known prior to conducting the inspection. The operator can maneuver the apparatus 21 to that location with input from the cable length tracker 51. Also, the video cameras 75 can provide a visual aid for the operator to properly position transducers 109, 117, on opposite sides of the next weld 52. Alternatively, a weld or flaw detector (not shown) can provide an electronic indication for the operator to properly position the transducers. For example, transducers such as the ultrasonic wall inspection transducers 121 can be used to detect the location of the welds 52 because the density of the weld material is different than the density of the material forming the drilling riser pipe 15.

The operator vertically repositions the inspection apparatus 21 to the next weld inspection site in the next weld inspection area to perform another weld inspection, as described above. The rotating TOFD module 33, weld volume inspection transducers 109 and weld root inspection transducers 117, are preferably rotated no more than one full revolution, i.e., 180 degrees, in one direction at the first inspection site and then rotated back that same amount in the opposite direction at the next inspection site. Where the TOFD module 33 includes two pairs of TOFD transducers 109, each pair of TOFD transducers 109 will sweep and measure 180 degrees, thus, covering all 360 degrees of weld inspection site during the 180 degree rotation. Similarly, each pair of shear wave transducers 117, if similarly implemented, will correspondingly also sweep 180 degrees. There is no need to rotate more than 180 degrees if the inspection apparatus 21 has two pairs of TOFD transducers 109. If the inspection apparatus 21 had only a single pair of TOFD transducers 109, then it would be necessary to rotate the TOFD module 33 one full revolution. Rotation more than one revolution is not needed and would tend to twist lines leading to the TOFD module 33 more than desired.

Once the inspection of the first weld inspection site is completed, the operator optionally may leave the TOFD module 33 in the 180 degree rotated position that existed at the conclusion of inspecting the first weld inspection site. At the next weld inspection site, the operator can inspect the site by rotating the TOFD module 33 in the opposite direction for 180 degrees. Once the operator reaches the opposite end, all of the welds 52, normally three per section of drilling riser pipe 15, will have been inspected, with the data recorded in either the CPU/data convert module 37 or a memory storage unit within or associated with the controller 43 (FIG. 7).

With the inspection of the drilling riser pipe 15 complete, the operator extracts any data not extracted real-time from the inspection apparatus 21 that is saved in the CPU/memory data convert module 37. The operator analyzes the data to determine whether a specific section of the drilling riser pipe 15 requires additional inspection and repair based upon the severity of any determined defects, if one so exists. If such defect is determined that is severe enough to warrant additional inspection and repair, advantageously the operator need only recover those sections of the drilling riser pipe 15 determined to have such a severe defect, and need only incidentally recover those sections located above the lowest section of those sections determined to require recovery. That is, the entire drilling riser 15 need not be recovered, only those affected sections and those necessary to gain access to the affected sections.

The invention has significant advantages. Deployment of the apparatus in a deployed drilling riser allows operators and drilling contractors to inspect the riser without the need to recover the riser. This avoids transporting the riser pipe sections to land, stripping the buoyant members and auxiliary lines then inspecting the pipes from the exterior. Inspecting internally avoids problems encountered due to external coatings. Because of the coupling liquid, the interiors of the riser sections do not have to be spotlessly clean for the inspection to be valid. Performing the weld tests and the corrosion tests with the same unit reduces the amount of equipment required and also saves time in that it can be done during one trip through the riser section. Rotating the inspection unit no more than one full turn allows the wires to be connected directly between the unit and the exterior without over twisting them. There is no need for electrical slip rings and rotational type manifolds. In the event a section of the riser is found to have defects, the information provided by the apparatus can be used to determine if the section is still fit for operational use or if it will have to be retrieved and replaced. In the event that the riser system is exposed to any abnormal conditions while deployed, the apparatus can be used to make a quick, low-cost evaluation of the critical features of the deployed riser system. The information provided by the apparatus will allow an operator or contractor to determine if the riser system should be recovered or if drilling operations can continue. In the event it is determined that the riser should be recovered, the apparatus can pinpoint which sections should receive a full topside evaluation. Drilling operations can resume with less down time, as only affected sections and those above those sections need be recovered, and only affected sections need be removed from service.

In the drawings and specification, there have been disclosed a typical preferred embodiment of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification. For example, the centralizer was shown to comprise a plurality of straps where wheels could also be instead utilized. Additionally, the tool housing was shown as a solid cylindrical housing but could instead be of another geometric shape or even not be of a solid form. Also for example, the wall thickness module can be used in place of the video module as an alternate methodology of both visualizing and detecting the location of a weld as the density of the weld material is different than the riser material. Also for example, the apparatus can be deployed without the TOFD module or can be deployed without the wall thickness module in accordance with the needs of the user.

That claimed is:

1. A method of inspecting a drilling riser pipe, the method comprising the steps of:
   (a) deploying an inspection apparatus into a drilling riser pipe while oriented upright, the inspection apparatus including at least one acoustical transducer;
   (b) centralizing the apparatus in the drilling riser pipe with the transducer spaced inward from a wall of the riser by a clearance;
   (c) providing a liquid in the clearance;
   (d) periodically causing the transducer to emit an acoustical signal through the liquid in the clearance and into the wall of the drilling riser and detecting a return acoustical signal from the wall of the drilling riser;
   wherein step (a) further comprises placing the transducer within a housing, and wherein step (d) further comprises emitting the acoustical signal through the housing.

2. The method according to claim 1, comprising the step of flushing an inner diameter of the drilling riser pipe with a fluid prior to deploying the inspection apparatus.

3. The method according to claim 1, wherein:
   the at least one transducer of step (a) further comprises a plurality of fixedly mounted non-rotating wall inspection transducers; and step (d) comprises:
   transmitting acoustical signals and receiving at least a portion of the acoustical signals from the wall inspection transducers, and thereby determining a wall thickness of the riser pipe.

4. The method according to claim 1, wherein the at least one transducer of step (a) comprises:
   a TOFD transmitter transducer and a TOFD receiver transducer positioned adjacent to and spaced apart from the first TOFD transmitter transducer along a longitudinal axis of the inspection apparatus; and
   step (d) comprises transmitting an acoustical signal with the TOFD transmitter transducer through a weld volume, and receiving a portion of the acoustical signal reflected from the weld volume with the TOFD receiver transducer.

5. A method of inspecting a drilling riser pipe, the method comprising the steps of:
   (a) deploying an inspection apparatus into a drilling riser pipe while oriented upright, the inspection apparatus including a housing containing a plurality of wall inspection transducers, a TOFD transmitter transducer and a TOFD receiver transducer positioned adjacent to and spaced apart from the first TOFD transmitter transducer along a longitudinal axis of the inspection apparatus;
   (b) lowering the apparatus in the drilling riser pipe; and
   (c) providing a liquid in the clearance;

(d) with the wall inspection transducers, transmitting acoustical signals through the wall of the housing and the liquid in the riser pipe and receiving at least a portion of the acoustical signals through the liquid in the clearance, and thereby determining a wall thickness of the riser pipe; and (e) positioning the TOFD transmitter and TOFD receiver transducer on opposite sides of a girth weld in the riser pipe, then transmitting an acoustical signal with the TOFD transmitter transducer through the wall of the housing and a volume of the weld, and receiving a portion of the acoustical signal reflected from the volume of the weld with the TOFD receiver transducer, and thereby detecting defects in the weld.

6. The method according to claim 5, wherein step (d) is performed without rotating the wall inspection transducers.

7. A method of inspecting a drilling riser, the method comprising the steps of:
   (a) lowering the drilling riser from a platform into seawater and allowing the seawater to enter the riser;
   (b) deploying an inspection apparatus into the drilling riser, the inspection apparatus including at least one acoustical transducer placed within a housing;
   (c) centralizing the apparatus in the drilling riser with the transducer spaced inward from a wall of the riser by an annular clearance;
   (d) periodically causing the transducer to emit an acoustical signal through the housing and through the seawater in the annular clearance and into the wall of the drilling riser and detecting a return acoustical signal from the wall of the drilling riser; and
   filling the housing with a liquid and equalizing pressure within the housing with hydrostatic pressure of seawater in the riser.

8. The method according to claim 7, wherein the at least one transducer of step (b) further comprises:

a TOFD transmitter transducer and a TOFD receiver transducer positioned adjacent to and spaced apart from the first TOFD transmitter transducer along a longitudinal axis of the inspection apparatus; and
   step (d) comprises transmitting an acoustical signal with the TOFD transmitter transducer through a volume of a girth weld, and receiving a portion of the acoustical signal reflected from the volume of the weld with the TOFD receiver transducer.

9. The method according to claim 7, wherein: the at least one transducer of step (a) further comprises a plurality of fixedly mounted non-rotating wall inspection transducers; and step (d) comprises:
   transmitting acoustical signals and receiving at least a portion of the acoustical signals from the wall inspection transducers, and thereby determining a wall thickness of the riser pipe.

10. The method according to claim 7, wherein the at least one transducer of step (b) comprises:
    a plurality of wall inspection transducers, a TOFD transmitter transducer, and a TOFD receiver transducer positioned adjacent to and spaced apart from the first TOFD transmitter transducer along a longitudinal axis of the inspection apparatus; and
    step (d) comprises transmitting acoustical signals and receiving at least a portion of the acoustical signals from the wall inspection transducers, and thereby determining a wall thickness of the riser pipe, and transmitting an acoustical signal with the TOFD transmitter transducer through a volume of a girth weld, and receiving a portion of the acoustical signal reflected from the volume of the weld with the TOFD receiver transducer.

* * * * *